(12) United States Patent
Gehrke

(10) Patent No.: US 8,648,227 B2
(45) Date of Patent: Feb. 11, 2014

(54) METHOD FOR EXTRACTING PURE STYRENE FROM A PYROLYSIS BENZINE FRACTION

(75) Inventor: Helmut Gehrke, Bergkamen (DE)

(73) Assignee: Thyssenkrupp Uhde GmbH, Dortmund (DE)

( * ) Notice: Subject to any disclaimer, the term of this patent is extended or adjusted under 35 U.S.C. 154(b) by 743 days.

(21) Appl. No.: 11/922,517

(22) PCT Filed: May 24, 2006

(86) PCT No.: PCT/EP2006/004918
§ 371 (c)(1),
(2), (4) Date: Aug. 12, 2009

(87) PCT Pub. No.: WO2006/136255
PCT Pub. Date: Dec. 28, 2006

(65) Prior Publication Data
US 2009/0306445 A1    Dec. 10, 2009

(30) Foreign Application Priority Data
Jun. 23, 2005   (DE) .......................... 10 2005 029 643

(51) Int. Cl.
C07C 7/08       (2006.01)
C07C 5/08       (2006.01)
(52) U.S. Cl.
USPC ........... 585/807; 585/258; 585/259; 585/264; 585/802; 585/804; 585/805; 585/806

(58) Field of Classification Search
USPC ......... 585/802, 804, 805, 806, 807, 258, 259, 585/264, 266
See application file for complete search history.

(56) References Cited

U.S. PATENT DOCUMENTS

| 2,799,627 | A | * | 7/1957 | Haensel ........................... 208/96 |
| 3,684,665 | A | * | 8/1972 | Abe et al. ........................ 203/9 |
| 3,763,015 | A | * | 10/1973 | Morimoto et al. ................ 203/9 |
| 3,801,615 | A | * | 4/1974 | Chuang .......................... 556/401 |
| 4,596,655 | A | * | 6/1986 | van Eijl ......................... 208/348 |
| 5,849,982 | A | * | 12/1998 | Lee et al. ....................... 585/833 |
| 6,927,314 | B1 | * | 8/2005 | Schultz et al. ................ 585/734 |
| 2004/0011706 | A1 | * | 1/2004 | Kaibel et al. ................... 208/347 |

* cited by examiner

Primary Examiner — In Suk Bullock
Assistant Examiner — Bradley Etherton
(74) Attorney, Agent, or Firm — Jonathan Myers; Andrew Wilford

(57) ABSTRACT

The invention relates to a method for extracting styrene, having a polymerization quality, from pyrolysis benzol fractions containing styrene by means of extractive distillation. The pyrolysis benzol fraction is separated in a separating wall column in a $C_8$-core fraction, a $C_7$ fraction and a $C_{9+}$-fraction, the obtained $C_8$-core fraction is subjected to selective hydrogenation of the phenylacetylene $C_8H_6$ which it contains. Subsequently, the obtained $C_8$-fraction undergoes extractive-distillative separation in a styrene fraction and a fraction which is low in styrene.

2 Claims, 2 Drawing Sheets

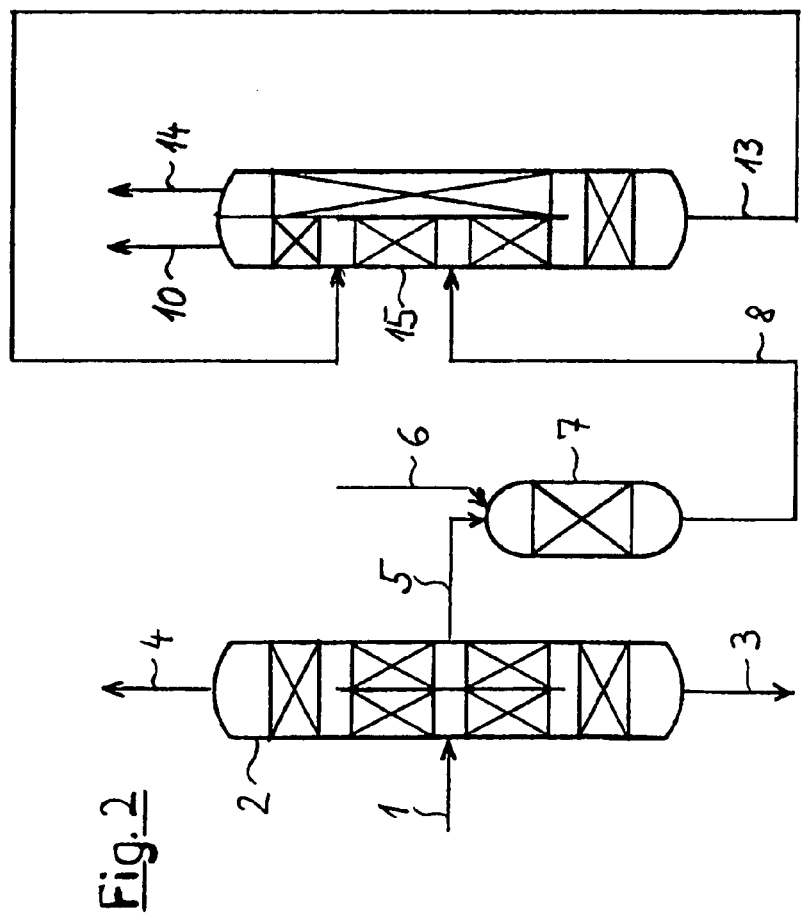

METHOD FOR EXTRACTING PURE STYRENE FROM A PYROLYSIS BENZINE FRACTION

BACKGROUND OF THE INVENTION

The invention relates to an improved process for the production of pure styrene from a pyrolysis gasoline fraction. Processes used to recover pure styrene of polymerisation grade from pyrolysis benzene fractions by extractive distillation are known from the documents listed hereafter: U.S. Pat. No. 3,684,665 by Toray and publications by Sato, Hydrocarbon Processing, May 1973, pages 141 ff, Morimoto et al., Bulletin of the Japan Petroleum Institute, Vol. 16, No. 1, May 1974, pages 38 ff, Gentry et al., Hydrocarbon Processing, June 1997, pages 73 ff., Emmrich et al., Int. J. of Hydrocarbon Engineering, Vol. 3, No. 9, October 1998, pages 62 ff, and Gentry et al., Hydrocarbon Processing, June 2004, pages 62 ff.

The state-of-the-art standard method encompasses the following processing steps:
(1) Separation of a $C_{7-}$ fraction as top fraction in a first distillation column and recovery of a $C_{8+}$ fraction as bottom fraction;
(2) Separation of a $C_{9+}$ fraction in the bottom of a second distillation column and recovery of a $C_8$ fraction at the column top;
(3) Selective hydrogenation of phenylacetylene in the $C_8$ fraction;
(4) Feeding the selectively hydrogenated $C_8$ fraction to an extractive distillation column and performance of the distillation to recover a styrene solvent fraction in the bottom and a fraction poor in styrene at the column top;
(5) Post-treatment of the styrene fraction to remove chromophores;
(6) Final treatment of the styrene fraction that has undergone post-treatment to remove by-products formed during post-treatment.

Step (3) of the selective hydrogenation of phenylacetylene is required to remove this component from the input stream to the extractive distillation. Phenylacetylene (=phenylethine) like styrene is an unsaturated compound. Its boiling point is approx. 142.4° C., i.e. very close to the boiling point of styrene (145.8° C.). Hence, a simple distillative separation of styrene is impossible. On account of its polarity, phenylacetylene cannot be removed by extractive distillation from styrene even in the presence of a selectively acting solvent, as the affinity of phenylacetylene to the selectively acting solvent is stronger than that of styrene to the said solvent. In this case, phenylacetylene together with styrene would be obtained as extract from such an extractive distillation.

The specification of pure styrene prescribes that the phenylacetylene content of pure styrene must not exceed a certain limit value. It is therefore necessary to remove the phenylacetylene from the styrene-bearing stream upstream of the extractive distillation unit. One method of such a removal is selective hydrogenation (3). In this process step, phenylacetylene is converted to styrene and/or ethyl benzene with the aid of hydrogen. A typical embodiment of this process step is to hydrogenate the phenylacetylene during the liquid phase at elevated pressure and under moderate temperature conditions. A catalyst is also required for this step. The specialist skilled in the art, as a rule, makes use of a noble metal catalyst (e.g. Pt or Pd) which is applied to a carrier material (such as $Al_2O_3$, $SiO_2$ or $TiO_2$).

With regard to the hydrogenation conditions, the pressure, temperature, retention time and catalyst quantity are optimised in such a manner that the phenylacetylene content of the reactor effluent reaches so low a level that during further styrene recovery the remaining phenylacetylene content of the styrene does not exceed the limit value and that the styrene loss due to overhydrogenation is minimised.

The following post-treatment methods in accordance with step (5) are known: U.S. Pat. No. 3,763,015 describes the treatment with a 60% nitric acid $HNO_3$ and DE 198 53 916 the treatment with maleic acid anhydride (MSA). The disadvantage of the two said methods, however, is that further chemicals are in fact required for post-treatment, the high equipment expenditure for the necessary reaction vessels and reprocessing steps as well as the higher styrene loss due to the treatment with $HNO_3$ or MSA, respectively, mainly caused by styrene polymerisation.

The said post-treatment is required because the styrene product obtained by step 0 is in fact in line with ASTM D-2827 requirements for the impurities contained, but it is not in accordance with the requirement for the colour of the product. This is set forth particularly in publications by Sato 1973, Morimoto 1974 and Emmrich et al., 1998. The above-mentioned ASTM code requires that the colour be ≤10 mg Pt/l (according to ASTM D-1209). The styrene product obtained by extractive distillation, however, has a light up to dark yellowish coloration, depending on the origin of the pyrolysis gasoline. This coloration is primarily due to the presence of 1,3-cyclopentadiene derivatives or other polyunsaturated, conjugated systems.

These are typical substances of the said group:
5-methylene-1,3-cyclopentadiene (fulvene)

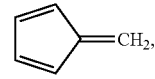

5-ethylidene-1,3-cyclopentadiene (6-methylfulvene),

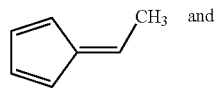

5-(1-methylethylidene)-1,3-cyclopentadiene (6,6-dimethylfulvene).

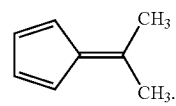

In general, the fulvenes constitute groups with the following parent substance:

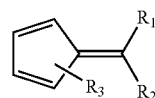

With $R_1$ = H, $CH_3$, $C_2H_5$, $C_3H_7$ or $C_4H_9$
With $R_2$ = H, $CH_3$, $C_2H_5$, $C_3H_7$ or $C_4H_9$
With $R_3$ = H, $CH_3$, $C_2H_5$, $C_3H_7$ or $C_4H_9$ These components and other non-cyclic, conjugated dienes and trienes are highly non-saturated components and absorb light in the visible area on account of their conjugated double-bond system. That is why these components have an intense coloration. Fulvenes, other cyclopentadiene derivates as well as further coloured, conjugated systems are hereinafter referred to as "chromophores". A characteristic feature of the chromophores is that their molecules encompass chromophore groups. "Chromophore groups" are understood to mean such groups of atoms within a molecule that absorb light in the visible area. Fulvenes and other chromophores form during naphtha steam cracking. The boiling point of the fulvene parent substance is approx. 60° C. at atmospheric pressure and that of 6,6-dimethylfulvene is approx. 160° C.

On account of the boiling point of the chromophores, one may come to the conclusion that it would be preferable either to separate them with the $C_{7-}$ fraction in the primary distillation unit (step (1)) or to remove them with the raffinate fraction, poor in styrene, from the styrene in the extractive distillation unit (step (2)). Conjugated double-bond systems, such as those of the above-mentioned chromophores, are capable of reacting by way of a Diels-Alder reaction with dienophiles, in this case particularly with olefins. The compounds thus formed have higher boiling points than the components undergoing the reaction. The products originating from this reaction are hereinafter referred to as "Diels-Alder products". The Diels-Alder reaction is of the reversible type so that the Diels-Alder products can decompose into the initial components, i.e. in this case the compounds with the conjugated double bonds and olefins.

The chromophores are "masked" as a result of the Diels-Alder reaction. Chromophores which initially were of the low-boiling type and should have been removable with the $C_{7-}$ fraction in the primary distillation, remain in the $C_{8+}$ fraction, which again is distilled in a second distillation column. In this step, part of the Diels-Alder products are re-converted into chromophores and the corresponding dienophiles as a result of the high temperatures and the relatively prolonged retention time in the column bottom. Hence, the chromophores enter the $C_8$ fraction and, in turn, part of the chromophores in the $C_8$ fraction react with olefins to form Diels-Alder products. This phenomenon in particular occurs in the case of reflux vessels or buffer tanks for intermediate products, for example. These further Diels-Alder products again mask the chromophores. Thus it becomes possible that the chromophores masked as Diels-Alder products can penetrate the stripping column of the extractive distillation unit and here they are re-converted into their initial components, i.e. chromophores and olefins, because of the high temperatures especially prevailing in the stripping zone and the bottom of the column. In spite of their boiling point location, a certain part of the chromophores contained in the raw pyrolysis gasoline consequently enter the styrene fraction originating from the extractive distillation and cause a coloration of the product.

BRIEF SUMMARY OF THE INVENTION

The objective of the invention, therefore, is to provide a process for the recovery of colourless polymerisation-grade styrene from pyrolysis benzene fractions, hence a method that does not require a final step for decolorisation of the pure styrene obtained by extractive distillation and that permits a cost-efficient production as a result of the treatment steps which can be avoided.

The objective of the invention as defined in the main claim is achieved by extractive distillation as follows:

The pyrolysis benzene fraction is fractionated in a divided-wall column so as to obtain a $C_8$ core fraction, a $C_{7-}$ fraction and a $C_{9+}$ fraction.

The $C_8$ core fraction thus obtained undergoes a selective hydrogenation of the phenylacetylene $C_8H_6$ contained in the said core fraction.

An extractive distillation of the $C_8$ core fraction obtained is carried out to extract a styrene fraction and a fraction poor in styrene.

The use of a divided-wall column permits a transfer of the low-boiling chromophores into the $C_{7-}$ fraction, yet without any possibility of masking as Diels-Alder products. On account of the low temperatures normally prevailing in the divided-wall column, the velocity of the exothermic Diels-Alder reaction is in fact low so that Diels-Alder products merely form in very small quantities and these minor amounts of Diels-Alder products are sent to the column bottom and removed there together with the $C_{9+}$ fraction.

If nevertheless Diels-Alder products are re-converted into their initial components in the divided-wall column bottom, the boiling point of the said products merely permits an entry into the $C_{7-}$ top fraction but not into the $C_8$ side stream. This also precludes any possible coloration of the final product originating from the extractive distillation, i.e. pure styrene. Therefore, post-treatment step (5) and downstream distillation step (6) included in the state-of-the-art configurations can be omitted, which also applies to the chemicals required for the said steps.

BRIEF DESCRIPTION OF THE DRAWINGS

The present invention is illustrated below on the basis of two typical embodiments. FIGS. 1 and 2 show simplified flowsheets of the process, each encompassing a primary distillation in a divided-wall column, a selective hydrogenation and an extractive distillation, the latter being illustrated as conventional type in FIG. 1 and as a further divided-wall column in FIG. 2.

DETAILED DESCRIPTION OF THE INVENTION

Figure 1:
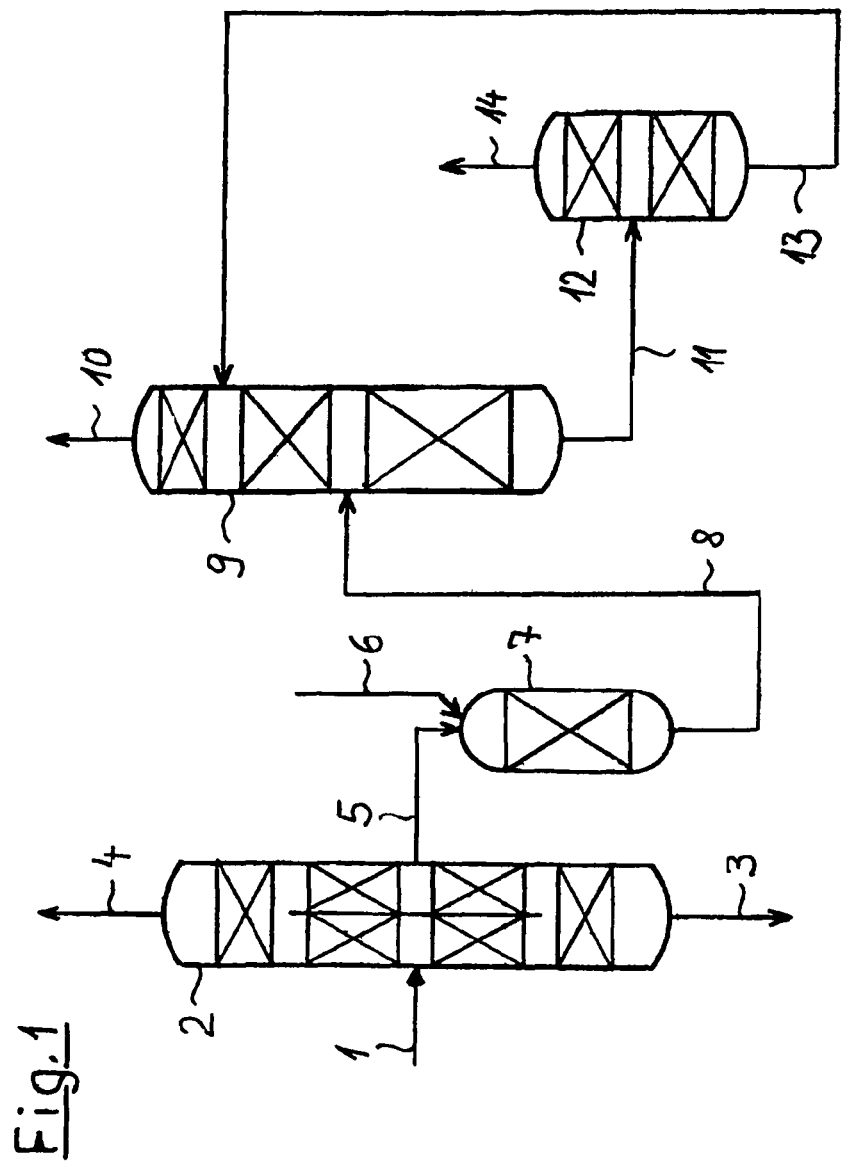

Raw pyrolysis gasoline 1 is fed on the side equipped with an insert tray in divided-wall column 2, in which the primary distillation takes place. The following products are withdrawn: $C_{9+}$ fraction 3 as bottom product, $C_{7-}$ fraction 4 as top product and $C_8$ core cut 5 as centre product. The latter together with hydrogen 6 undergoes selective hydrogenation 7.

FIG. 1 shows that hydrogenated $C_8$ core cut 8 withdrawn from selective hydrogenation 7 is piped to extractive distillation column 9 from the top of which a styrene desaturated $C_8$ core cut 10 is withdrawn and that styrene stream 11 dissolved in an extraction agent is piped from the bottom to stripping column 12 in which extraction agent 13 is recovered to be subsequently used in extractive distillation column 9, whereas pure styrene 14 is withdrawn at the top.

FIG. 2 shows the option according to which hydrogenated $C_8$ core cut 8 withdrawn from selective hydrogenation 7 is piped to extractive-distillation divided wall-type column 15, with the upper right side of the divided wall being closed, the stripper being integrated into the bottom as well as into the right side of the divided-wall column, pure styrene 14 being withdrawn from the lateral outlet located in the right section of the divided wall, recovered extraction agent 13 being fed above the divided wall section carrying the hydrocarbon feed tray, and styrene desaturated $C_8$ core cut 10 being withdrawn at the top of extractive-distillation divided wall-type column 15.

Table 1 overleaf details the typical process conditions of the individual steps of the process in accordance with the present invention:

TABLE 1

| | Parameter range | Preferred parameter range | Example |
|---|---|---|---|
| *Primary distillation Divided-wall column* | | | |
| Temperature at top | 50-120° C. | 50-100° C. | 100° C. |
| Temperature at bottom | 100-150° C. | 120-140° C. | 128° C. |
| Pressure at top | 100-400 mbar | 200-300 mbar | 300 mbar |
| *Selective hydrogenation* | | | |
| Reaction temperature | 20-60° C. | 20-40° C. | 25° C. |
| Partial pressure of hydrogen | 1-20 bar | 5-10 bar | 8 bar |
| Space velocity (LHSV) | 1-20 l/(l·h) | 5-10 l/(l·h) | 8 l/(l·h) |
| Operational mode | | liquid phase | liquid phase |
| Catalyst | | noble metal-based | Pd on $Al_2O_3$ |
| *Extractive distillation (acc. to FIG. 1)* | | | |
| Temperature at top | 20-120° C. | 50-80° C. | 77° C. |
| Temperature at bottom | 100-150° C. | 120-140° C. | 129° C. |
| Pressure at top | 10-400 mbar | 50-200 mbar | 90 mbar |
| Circulation rate | 1-20 kg solvent per kg feed | 5-15 kg solvent per kg feed | 8.8 kg solvent per kg feed |
| *Stripping column (acc. to FIG. 1)* | | | |
| Temperature at top | 20-120° C. | 50-80° C. | 67° C. |
| Temperature at bottom | 100-180° C. | 140-160° C. | 150° C. |
| Pressure at top | 10-400 mbar | 50-200 mbar | 80 mbar |
| *Extractive distillation (acc. to FIG. 2)* | | | |
| Temperature at top (raffinate side) | 20-120° C. | 50-80° C. | 67° C. |
| Temperature at top (extract side) | 20-120° C. | 50-80° C. | 70° C. |
| Temperature at bottom | 100-180° C. | 120-160° C. | 150° C. |
| Pressure at top | 10-400 mbar | 50-200 mbar | 80 mbar |

Pressure data in terms of abs. pressure!

The invention claimed is:

1. A process for the production of colorless styrene of polymerization grade from a pyrolysis gasoline fraction containing $C_7$-, $C_8$ and $C_{9+}$ hydrocarbons, wherein the $C_7$-hydrocarbons include cyclopentadiene chromophores and wherein the $C_8$ hydrocarbons include phenylacetylene, by fractional and extractive distillation, which consists essentially of the steps of:
    (a) fractionally distilling the pyrolysis gasoline fraction containing $C_7$-, $C_8$ and $C_{9+}$ hydrocarbons, in a divided-wall column having a top, a center and a bottom, at a temperature too low for the cyclopentadiene chromophores to undergo a Diels-Alder reaction with olefins to form Diels-Alder products in which the cyclopentadiene chromophores are masked by olefins, but which can decompose into the initial reactants, to obtain at the top a $C_7$- hydrocarbon fraction including cyclopentadiene chromophores, to obtain at the center a $C_8$ core hydrocarbon fraction including styrene and phenylacetylene, said $C_8$ core hydrocarbon fraction free of the cyclopentadiene chromophores masked by olefins, and to obtain at the bottom a $C_{9+}$ hydrocarbon fraction;
    (b) selectively hydrogenating phenylacetylene within the $C_8$ core hydrocarbon fraction; and following step (b);
    (c) extractively distilling the $C_8$ core hydrocarbon fraction to extract a colorless styrene of polymerization grade fraction and a fraction poor in styrene, wherein steps (a), (b) and (c) are the only required steps carried out to obtain the colorless styrene of polymerization grade from the pyrolysis gasoline fraction.

2. The process for the production of colorless styrene defined in claim 1 wherein according to step (a) the temperature of the fractional distillation at the top of the fractional distillation column is 50 to 100° C.

* * * * *

UNITED STATES PATENT AND TRADEMARK OFFICE
CERTIFICATE OF CORRECTION

PATENT NO.       : 8,648,227 B2                                      Page 1 of 1
APPLICATION NO. : 11/922517
DATED            : February 11, 2014
INVENTOR(S)      : Helmut Gehrke It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1357 days.

Signed and Sealed this
Twenty-ninth Day of September, 2015

Michelle K. Lee
*Director of the United States Patent and Trademark Office*